(12) United States Patent
Fattinger et al.

(10) Patent No.: US 10,533,972 B2
(45) Date of Patent: Jan. 14, 2020

(54) FLUIDIC DEVICE WITH FLUID PORT ORTHOGONAL TO FUNCTIONALIZED ACTIVE REGION

(71) Applicant: Qorvo US, Inc., Greensboro, NC (US)

(72) Inventors: Gernot Fattinger, Sorrento, FL (US); Rio Rivas, Bend, OR (US)

(73) Assignee: QORVO US, INC., Greensboro, NC (US)

( * ) Notice: Subject to any disclaimer, the term of this patent is extended or adjusted under 35 U.S.C. 154(b) by 419 days.

(21) Appl. No.: 15/341,330

(22) Filed: Nov. 2, 2016

(65) Prior Publication Data

US 2017/0122912 A1    May 4, 2017

Related U.S. Application Data

(60) Provisional application No. 62/249,515, filed on Nov. 2, 2015.

(51) Int. Cl.
*G01N 29/02* (2006.01)
*H03H 9/02* (2006.01)
*H03H 9/17* (2006.01)

(52) U.S. Cl.
CPC . *G01N 29/022* (2013.01); *G01N 2291/02466* (2013.01); *G01N 2291/0422* (2013.01)

(58) Field of Classification Search
None
See application file for complete search history.

(56) References Cited

U.S. PATENT DOCUMENTS

| 4,640,756 | A | 2/1987 | Wang et al. |
| 7,468,608 | B2 | 12/2008 | Feucht et al. |
| 7,784,329 | B2 * | 8/2010 | Martinoty ............. G01N 11/16 73/54.01 |
| 7,802,466 | B2 * | 9/2010 | Whalen ............. B01L 3/502776 73/54.41 |
| 8,409,875 | B2 | 4/2013 | Johal et al. |
| 2005/0148065 | A1 * | 7/2005 | Zhang ................... B82Y 15/00 435/287.2 |
| 2010/0313636 | A1 * | 12/2010 | Wakamatsu ......... G01N 29/022 73/64.53 |

(Continued)

OTHER PUBLICATIONS

Voiculescu, I. et al., "Acoustic Wave Based MEMS Devices for Biosensing Applications", Biosensors and Bioelectronics, vol. 33, pp. 1-9. (Year: 2012).*

(Continued)

*Primary Examiner* — Daniel S Larkin
(74) *Attorney, Agent, or Firm* — Mueting, Raasch & Gebhardt, P.A.

(57) ABSTRACT

A fluidic device includes at least one bulk acoustic wave (BAW) resonator structure with a functionalized active region, and at least one first (inlet) port defined through a cover structure arranged over a fluidic passage containing the active region. At least a portion of the at least one inlet port is registered with the active region, permitting fluid to be introduced in a direction orthogonal to a surface of the active region bearing functionalization material. Such arrangement promotes mixing proximate to a BAW resonator structure surface, thereby reducing analyte stratification, increasing analyte binding rate, and reducing measurement time.

12 Claims, 9 Drawing Sheets

(56) References Cited

U.S. PATENT DOCUMENTS

2017/0122911 A1* 5/2017 McCarron ............ G01N 29/036

OTHER PUBLICATIONS

Qorvo US, Inc., "Summary of Sales Activity of Predecessor to Applicant Concerning Tilted C-axis Aluminum Nitride Products," Unpublished, Jan. 10, 2017, 1 page.
Bjurström, J. et al., "Design and Fabrication of Temperature Compensated Liquid FBAR Sensors," IEEE Ultrasonics Symposium, Oct. 2-6, 2006, pp. 894-897.
Chen, Ying-Chung et al., "The Liquid Sensor Using Thin Film Bulk Acoustic Resonator with C-Axis Tilted AlN =Films," Journal of Nanomaterials, vol. 2013, Article ID 245095, 2013, 8 pages.
Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.
Groner, M. D. et al., "Gas diffusion barriers on polymers using $Al_2O_3$ atomic layer deposition," Applied Physics Letters, vol. 88, Jan. 31, 2006, pp. 051907-1 to 051907-3.
Lee, Chia-Yen et al., "Microfluidic Mixing: A Review," International Journal of Molecular Sciences, vol. 12, May 18, 2011, pp. 3263-3287.
Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.
Luo, J. K. et al., "Acoustic Wave Based Microfluidics and Lab-on-a-Chip," Modeling and Measurement Methods for Acoustic Waves and for Acoustic Microdevices, Chapter 21, Aug. 28, 2013, InTech, pp. 515-556.
Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.
Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.
Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.
Nirschl, Martin et al., "CMOS-Integrated Film Bulk Acoustic Resonators for Label-Free Biosensing," Sensors, vol. 10, No. 5, Apr. 27, 2010, pp. 4180-4193.
Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.
Miller, "The Stokes-Einstein Law for Diffusion in Solution," *Proceedings of the Royal Society of London. Series A, Containing Papers of a Mathematical and Physical Character* (1905-1934), Jan. 1924, 106(70):724-49.
Through Silicon Vias (TSV) for backside electrical connection are common in devices https://en.wikipedia.org/wiki/Through-sificon_via.

\* cited by examiner

FLUIDIC DEVICE WITH FLUID PORT ORTHOGONAL TO FUNCTIONALIZED ACTIVE REGION

STATEMENT OF RELATED APPLICATIONS

This application claims the benefit of provisional patent application Ser. No. 62/249,515, filed Nov. 2, 2015, the disclosure of which is hereby incorporated herein by reference in its entirety.

TECHNICAL FIELD

The present disclosure relates to fluidic devices incorporating acoustic resonators, including fluidic devices suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods used with biosensors may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, amplitude-magnitude, or phase characteristics of the acoustic wave device and can be correlated to a physical quantity being measured.

In the case of a piezoelectric crystal resonator, an acoustic wave may embody a bulk acoustic wave (BAW) propagating through the interior (or "bulk") of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves, and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes, as the particle vibration, or polarization, is neither purely parallel nor purely perpendicular to the propagation direction. The propagation characteristics of the respective modes depend on the material properties and propagation direction respective to the crystal axis orientations. Since shear waves exhibit a very low penetration depth into a liquid, a device with pure or predominant shear modes can operate in liquids without significant radiation losses (in contrast with longitudinal waves, which can be radiated in liquid and exhibit significant propagation losses). The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride [AlN] and zinc oxide [ZnO]. To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof. Conversely, a piezoelectric material grown with a c-axis orientation that is perpendicular relative to a face of an underlying substrate will enable a BAW resonator structure to exhibit a dominant longitudinal response upon application of an alternating current signal across electrodes thereof.

Typically, BAW devices are fabricated by micro-electromechanical systems (MEMS) fabrication techniques, owing to the need to provide microscale features suitable for facilitating high-frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Under typical operating conditions, flows in microfluidic passages or channels (also termed "microchannels") are laminar. Fluids in laminar flow tend to follow parallel streamline paths, such that the chaotic fluctuations of velocity that tend to homogenize fluids in turbulent flows are absent. Multiple fluids introduced in a standard microchannel generally will not mix with each other, except at a common interface between the fluids via diffusion, and the diffusion process is typically slow in comparison to the flow of fluid along a principal axis of a microfluidic channel. The same principles that inhibit rapid mixing of fluids flowing under laminar conditions in a microfluidic channel also affect the distribution of analytes contained in one or more fluids flowing within a microfluidic channel. Flux moves from regions of high concentration to regions of low concentration according to Fick's first law of diffusion; additionally, the flux rate is proportional to the concentration gradient difference. A hypothetical volume of fluid containing an analyte and advancing in a horizontal direction through a microfluidic channel having functionalization material arranged along a bottom surface of the channel may be modeled as a moving "stack" of horizontal fluid layers. Following passage in a horizontal direction over the functionalization material, a lowermost fluid layer of the stack will exhibit reduced or depleted analyte concentration due to binding of analyte with the functionalization material. But since diffusion is slow in a direction perpendicular to the direction of fluid flow through the microfluidic channel, and analyte needs to diffuse to a surface bearing functionalization material to bind, analyte present in fluid layers other than the lowermost fluid layer may not be available for binding with the functionalization material along the bottom surface of the channel within a reasonable period of time. Analyte concentration may remain stratified or inconsistently distributed within the channel until diffusion occurs. Additionally, large analyte molecules may require a long time to bind with functionalization material. Due to these considerations, analyte binding rate is limited, and an extended time may be necessary to complete measurement of a particular sample.

Accordingly, there is a need for fluidic devices incorporating bulk acoustic wave resonator structures, such as for biosensing or biochemical sensing applications, that overcome limitations associated with conventional devices.

SUMMARY

The present disclosure relates to a fluidic device including at least one bulk acoustic wave (BAW) resonator structure with a functionalized active region, and including at least one first port (e.g., inlet port) defined through a cover structure arranged over a fluidic passage containing the active region, wherein at least a portion of the at least one first port is registered with the active region. Such arrangement permits fluid to be introduced in a direction orthogonal to a surface of the active region that bears a functionalization material. The orthogonal fluid flow promotes mixing proximate to the functionalized active region, thereby increasing binding of analyte and reducing measurement time. One or more layers (e.g., a hermeticity layer, an interface layer, and/or a self-assembled monolayer) may be arranged between the top side electrode and the functionalization material. At least one second port (e.g., outlet port) may be provided in various configurations. Methods for biological or chemical sensing are further provided.

In one aspect, a fluidic device includes: a base structure comprising: (i) a substrate; (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and (iii) at least one functionalization material arranged over at least a portion of the active region; a wall structure arranged over at least a portion of the base structure and defining lateral boundaries of a fluidic passage arranged to receive a fluid and containing the active region; and a cover structure arranged over the wall structure and defining an upper boundary of the fluidic passage; wherein the cover structure defines at least one first port that is in fluid communication with the fluidic passage, and at least a portion of the at least one first port is registered with the active region.

In certain embodiments, the wall structure and the cover structure are embodied in a monolithic body structure. In certain embodiments, the wall structure and the base structure are embodied in a monolithic body structure. In certain embodiments, the cover structure comprises a cover layer, the wall structure comprises at least one wall layer, and the at least one wall layer is arranged between the base structure and the cover layer.

In certain embodiments, the fluidic device further includes at least one second port that is in fluid communication with the fluidic passage, wherein the at least one second port is defined through the base structure. In certain embodiments, the fluidic device further includes at least one second port that is in fluid communication with the fluidic passage, wherein the at least one second port is defined through the wall structure. In certain embodiments, the fluidic device further includes at least one second port that is in fluid communication with the fluidic passage, wherein the at least one second port is defined through the cover structure.

In certain embodiments, the fluidic device further includes a plurality of second ports in fluid communication with the fluidic passage, wherein each second port of the plurality of second ports is laterally displaced relative to the at least one first port.

In certain embodiments, the at least one bulk acoustic wave resonator structure comprises a plurality of bulk acoustic wave resonator structures. In certain embodiments, the plurality of bulk acoustic wave resonator structures is registered with the fluidic passage.

In certain embodiments, the base structure further comprises at least one acoustic reflector element arranged between the substrate and the at least one bulk acoustic wave resonator structure.

In certain embodiments, the substrate defines a recess arranged below the active region.

In certain embodiments, the piezoelectric material comprises a c-axis having an orientation distribution that is predominantly non-parallel to normal of a face of the substrate.

In certain embodiments, the at least one functionalization material comprises a specific binding material. In certain embodiments, the at least one functionalization material comprises a non-specific binding material.

In certain embodiments, the fluidic device further includes a self-assembled monolayer arranged between the at least one functionalization material and the top side electrode. In certain embodiments, the fluidic device further includes an interface layer arranged between the self-assembled monolayer and the top side electrode. In certain embodiments, the fluidic device further includes a hermeticity layer arranged between the interface layer and the top side electrode.

In another aspect, a method for biological or chemical sensing includes: supplying a fluid containing a target species to a fluidic device including a fluidic passage containing an active region of at least one bulk acoustic wave resonator structure, wherein at least a portion of the active region is overlaid with at least one functionalization material, wherein said supplying is configured to introduce the fluid through at least one first port registered with the active region to cause the fluid to enter the fluidic passage in a first direction normal to a planar surface of the active region and to cause at least some of the target species to bind to the at least one functionalization material; inducing a bulk acoustic wave in the active region; and sensing a change in at least one of an amplitude-magnitude property, a frequency property, or a phase property of the at least one bulk acoustic wave resonator structure to indicate at least one of presence or quantity of target species bound to the at least one functionalization material.

In certain embodiments, the fluidic passage is in fluid communication with at least one second port that is laterally displaced relative to the at least one first port, and said supplying is further configured to cause at least a portion of the fluid to transit through the fluidic passage in a lateral direction and thereafter exit the fluidic passage through the at least one second port.

In certain embodiments, the at least one bulk acoustic wave resonator structure includes a top side electrode, a piezoelectric material, and a bottom side electrode arranged over a substrate; the piezoelectric material comprises a c-axis having an orientation distribution that is predominantly non-parallel to normal of a face of the substrate; a portion of the piezoelectric material is arranged between the top side electrode and the bottom side electrode to form the active region; and the inducing of a bulk acoustic wave in the active region comprises applying an alternating current signal across the top side electrode and the bottom side electrode, whereby the at least one bulk acoustic wave resonator structure exhibits a dominant shear response upon application of the alternating current signal.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 11 is essentially the same as FIG. 6 except that the cover and walls are shown as monolithic in FIG. 11.

DETAILED DESCRIPTION

Figure 1:
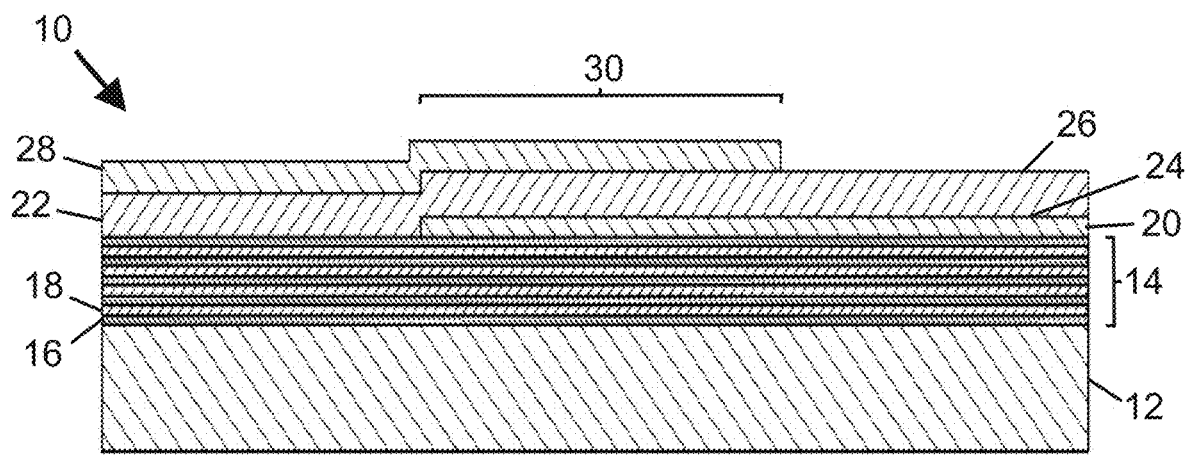
FIG. 1 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure relates to a fluidic device including at least one bulk acoustic wave (BAW) resonator structure with a functionalized active region, and including at least one first port (e.g., inlet port) defined through a cover structure arranged over a fluidic passage containing the active region, wherein at least a portion of the at least one first port is registered with the active region. Fluid is introduced in a direction orthogonal to a surface of the active region that bears a functionalization material. Fluid flow changes direction proximate to the active region (e.g., from a vertical direction to a lateral direction) before traveling to at least one second port (e.g., outlet port). This flow pattern promotes mixing proximate to the functionalized active region, thereby reducing stratification of analyte, increasing binding of analyte, and reducing measurement time. One or more layers (e.g., a hermeticity layer, an interface layer, and/or a self-assembled monolayer) may be arranged between the top side electrode and the functionalization material. The at least one second port (e.g., outlet port) may be provided in various configurations. Methods for biological or chemical sensing are further provided.

To enable a change in flow direction, a functionalized surface of an active region of a BAW resonator structure may be arranged in a fluidic passage, whereby fluid is introduced through at least one first port (e.g., fluidic inlet port) into the fluidic passage, and the at least one first port is arranged above and registered with the active region. In certain embodiments, the fluidic passage includes a width dimension extending beyond a width of the active region. In certain embodiments, lateral boundaries of the fluidic passage are defined by a wall structure arranged between a base structure (including a substrate and the BAW resonator structure) and a cover structure. In certain embodiments, the wall structure and the cover structure are integrated and embodied in a monolithic body structure. In other embodiments, the wall structure and the base structure may be integrated and embodied in a monolithic body structure.

In certain embodiments, at least one first port is substantially centered relative to an active region. In certain embodiments, only a portion of the at least one first port is arranged directly over an active region.

In certain embodiments, at least one first port comprises a width dimension that exceeds a width dimension of an active region. In other embodiments, the active region comprises a width dimension that exceeds a width dimension of the at least one first port. In either instance, at least a portion of the at least one first port may be registered with the active region.

In certain embodiments, at least one second port (e.g., fluidic outlet port) may be defined though a cover structure (e.g., comprising a cover layer). In certain embodiments, each fluidic outlet port may be laterally offset relative to an active region of a BAW resonator structure. In other embodiments, a portion of the at least one second port may overlap a portion of the active region.

In certain embodiments, at least one second port (e.g., fluidic outlet port) may be defined though a wall structure that is intermediately arranged between a cover structure and a base structure.

In certain embodiments, at least one second port (e.g., fluidic outlet port) may be defined through a base structure, including through a substrate and a piezoelectric material. In certain embodiments, at least one first port and at least one second port may be defined through the substrate and piezoelectric material via laser micromachining guided in a water jet. Other hole-defining methods may be used, including but not limited to etching or mechanical drilling.

In certain embodiments, multiple second ports may be provided to promote division or splitting of one or more fluid inlet flows to a larger number of fluid outlet flows.

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Such a c-axis orientation distribution enables creation of shear displacements at certain frequencies (which beneficially enables operation of a BAW resonator-based sensing device in liquid environments), and enables creation of longitudinal displacements at other frequencies (which may be useful to promote localized mixing). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein.

Before describing fluidic devices with inlet ports orthogonal to functionalized active regions, exemplary bulk acoustic wave MEMS resonator devices, associated layers useful for providing biochemical sensing utility, and fluidic devices incorporating MEMS resonator devices will be introduced.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with an active region of the BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

FIG. 1 is a schematic cross-sectional view of a portion of a bulk acoustic wave (BAW) MEMS resonator device 10 useable with embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, the piezoelectric material 22 comprises a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate 12. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or a functionalization material (which may include specific binding material or non-specific binding material).

Figure 2:
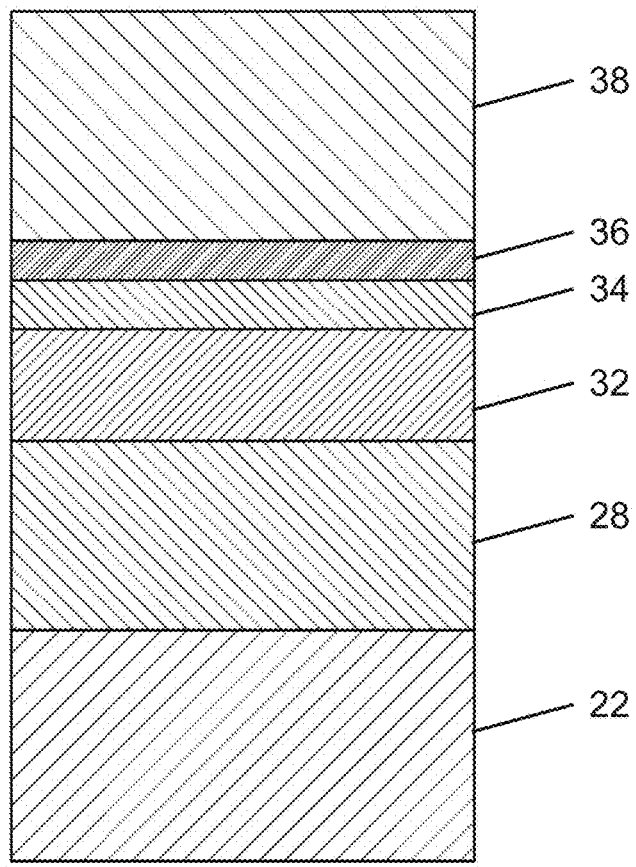
FIG. 2 is a schematic cross-sectional view of an upper portion of a BAW MEMS resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of the interface layer 34 to prevent localized attachment of one or more subsequently deposited layers, or (if applied over selected regions of the SAM 36 or functionalization material 38) to prevent analyte capture in regions not overlying the active region 30 of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide [$Al_2O_3$] or silicon nitride [SiN]. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a back bone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithographic masking and selective etching for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active areas of a multi-resonator structure (i.e., one or more resonator structures including multiple active regions), optionally in combination with one or more active areas that are devoid of specific binding materials to serve as comparison (or "reference") regions. In certain embodiments, a functionalization (e.g., bio-functionalization) material may provide non-specific binding utility.

Certain embodiments are directed to a fluidic device including multiple bulk acoustic wave (BAW) MEMS resonator structures as disclosed herein and including a fluidic passage (e.g., a channel, a chamber, or the like) arranged to conduct a liquid to contact at least one functionalization (e.g., specific binding) material arranged over at least one active region of the BAW MEMS resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of the microfluidic passage; in other embodiments, functionalization material may be applied over an active region of a bulk acoustic wave resonator structure following formation of the microfluidic passage.

Walls of a microfluidic passage may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic passage, and the integrally formed partial cover/wall structure may be applied (e.g., adhered or otherwise bonded) over at least a portion of a bulk acoustic wave resonator structure to enclose the at least one fluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 3:
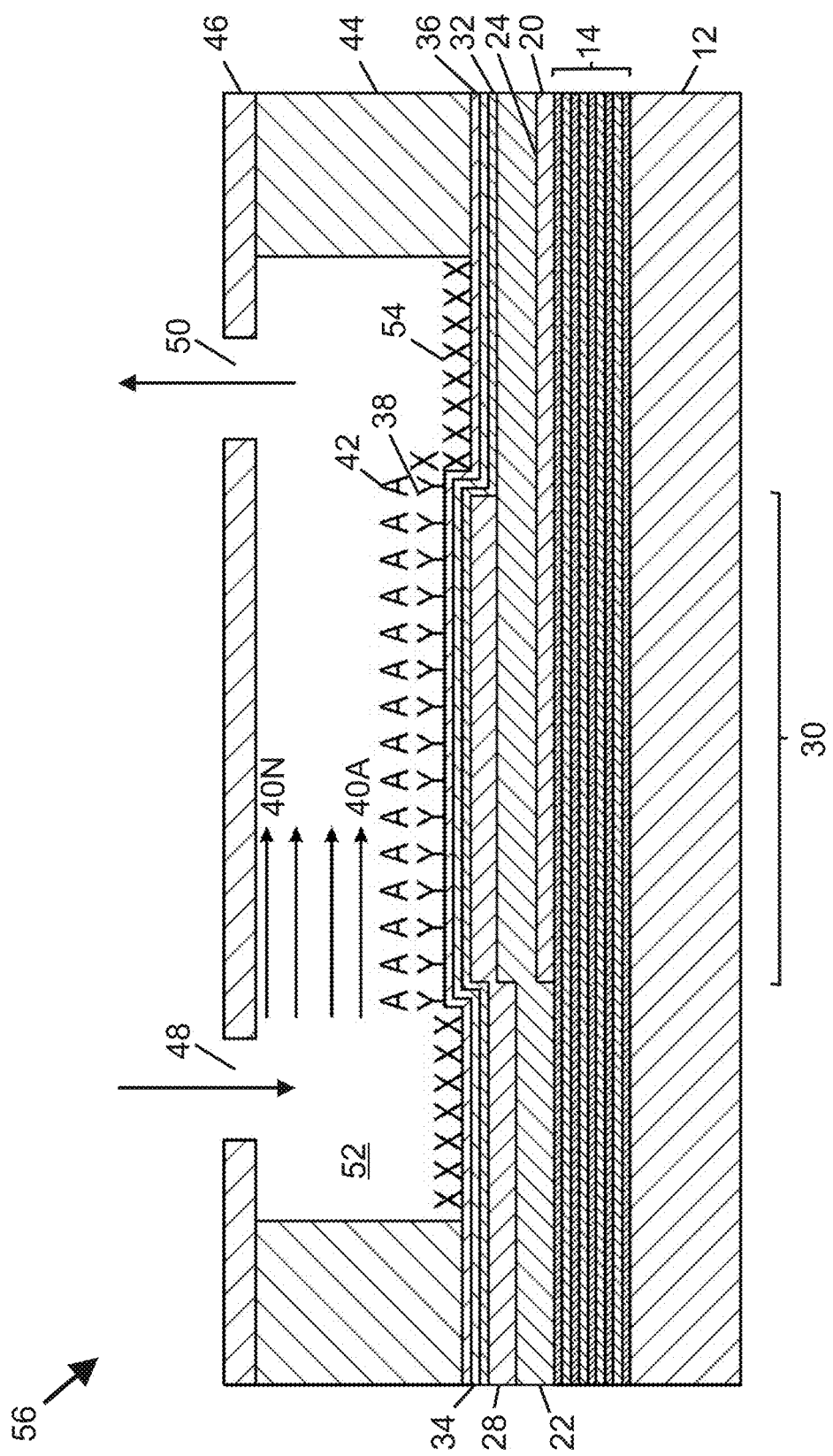
FIG. 3 is a schematic cross-sectional view of a portion of a fluidic device (e.g., a biochemical sensor device) including a fluidic passage bounded from below by a BAW resonator structure, bounded laterally by walls, and bounded from above by a cover or cap layer, with a self-assembled monolayer (SAM) arranged over the entire piezoelectric material and blocking material arranged over portions of the SAM non-coincident with an active region distal from fluidic ports defined in the cover or cap layer, to serve as a first comparison device intended to provide context for subsequently described embodiments of the disclosure.

FIG. 3 is a schematic cross-sectional view of a portion of a fluidic device 56 (e.g., a biochemical sensor device) including a fluidic passage 52 (which may be microfluidic in character) that is bounded from below by a bulk acoustic wave resonator structure including an active region 30, bounded laterally by walls 44, and bounded from above by a cover or cap layer 46 defining a fluidic inlet port 48 and a fluidic outlet port 50, with the fluidic device 56 serving as a first comparison device intended to provide context for subsequently described embodiments of the disclosure. The fluidic device 56 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the walls 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte. Walls 44 that are laterally displaced from the active region 30 extend upward from the SAM 36 to define lateral boundaries of the fluidic passage 52 containing the active region 30. The walls 44 may be formed of any suitable material, such as a laser-cut "stencil" layer of thin polymeric materials and/or laminate materials, optionally including one or more self-adhesive surfaces (e.g. adhesive tape). Optionally such walls 44 may be formed prior to deposition of the SAM 36, functionalization material 38, and chemical or biological blocking material 54 with an SU-8 negative epoxy resist or other photoresist material. The cover or cap layer 46 defining fluidic inlet and outlet ports 48, 50 is further provided to provide an upper boundary for the fluidic passage 52. The cover or cap layer 46 may be formed by defining fluidic inlet and outlet ports 48, 50 (e.g., via laser cutting or water jet cutting) in a layer of an appropriate material (e.g., a substantially inert polymer, glass, silicon, ceramic, or the like), and adhering the cover or cap layer 46 to top surfaces of the walls 44.

In use of the fluidic device 56, a fluid sample may be supplied through the fluidic inlet port 48 into the fluidic passage 52 over the active region 30 and then flow through the fluidic outlet port 50 to exit the fluidic passage 52. Due to the laminar nature of the fluid flow within the fluidic passage 52, the fluid volume may be modeled and behave as a "stack" of horizontal fluid layers including a lowermost fluid layer 40A and an uppermost fluid layer 40N. An analyte 42 contained in the lowermost fluid layer 40A of the fluid sample will tend to bind with functionalization material 38 arranged over the active region 30. Analyte contained in fluid layers above the lowermost fluid layer 40A (including the uppermost fluid layer 40N) may not be available to bind with the functionalization material 38, since diffusion of analyte (e.g., in a vertical direction) between the fluid layers 40A-40N may occur slowly. Assuming that sufficient analyte is present proximate to the lowermost fluid layer 40A to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte bound to the functionalization material 38.

Figure 4:
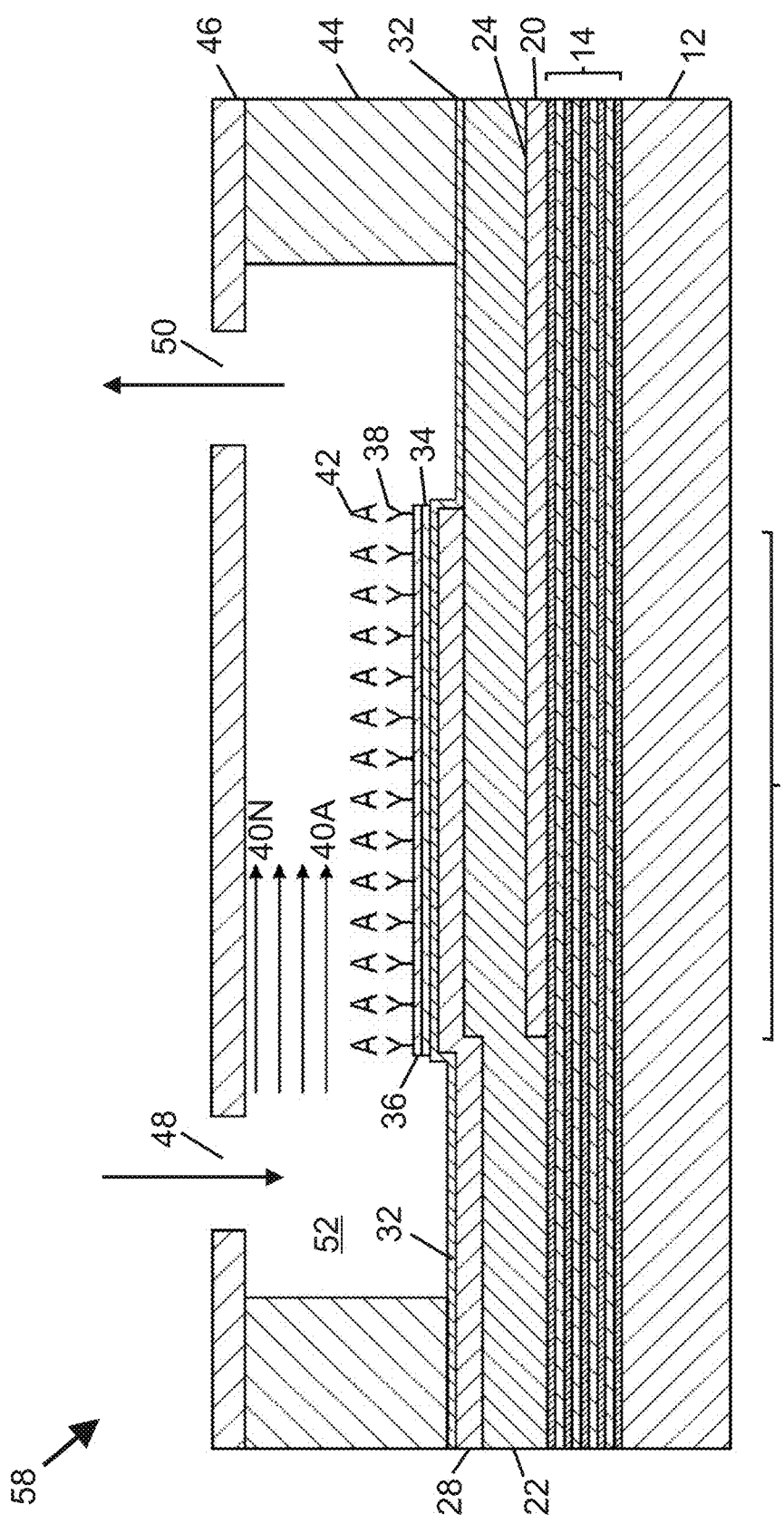
FIG. 4 is a schematic cross-sectional view of a portion of a fluidic device (e.g., a biochemical sensor device) including a fluidic passage bounded from below by a BAW resonator structure, bounded laterally by walls, and bounded from above by a cover or cap layer, with an interface layer, a SAM, and functionalization material arranged only over an active region distal from fluidic ports defined in the cover or cap layer, to serve as a second comparison device intended to provide context for subsequently described embodiments of the disclosure.

FIG. 4 is a schematic cross-sectional view of a portion of a fluidic device (e.g., a biochemical sensor device) 58 similar to the fluidic device 56 of FIG. 3, serving as a second comparison device intended to provide context for subsequently described embodiments of the disclosure. As compared to the fluidic device 56 of FIG. 3, the fluidic device 58 of FIG. 4 includes an interface layer 34 and a SAM 36 that are provided solely over an active region 30 instead of over an entirety of piezoelectric material 22. Such configuration may be provided by controlling lateral boundaries of the interface layer 34 (e.g., by photolithographic patterning and selective etching, for example). The fluidic device 58 includes a fluidic passage 52 that is bounded from below by a bulk acoustic wave resonator structure including the active region 30, bounded laterally by walls 44, and bounded from above by a cover or cap layer 46 defining a fluidic inlet port 48 and a fluidic outlet port 50. The fluidic device 58 includes a substrate 12 overlaid with an acoustic reflector 14, and a bottom side electrode 20 arranged generally below the piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. A hermeticity layer 32 is arranged over the top side electrode 28 and the piezoelectric material 22. The interface layer 34 and the SAM 36 are provided over a portion of the hermeticity layer 32 that is registered with the active region 30. The SAM 36 is overlaid with a layer of functionalization (e.g., specific binding) material 38 arranged to bind at least one analyte (e.g., analyte 42). Walls 44 that are laterally displaced from the active region 30 extend upward from the hermeticity layer 32 to define lateral boundaries of the fluidic passage 52 containing the active region 30. The cover or cap layer 46 defining a fluidic inlet port 48 and a fluidic outlet port 50 is provided over the walls 44 to provide an upper boundary for the fluidic passage 52. Operation of the fluidic device 58 of FIG. 4 is similar to the operation of the fluidic device 56 of FIG. 3. A volume of fluid may behave as a "stack" of horizontal fluid layers including a lowermost fluid layer 40A and an uppermost fluid layer 40N within the fluidic passage 52, wherein the lowermost fluid layer 40A is proximate to functionalization material 38 overlying the active region 30. Assuming the presence of sufficient analyte in the fluid (including the lowermost fluid layer 40A) when a bulk acoustic wave having a dominant shear component is induced in the active region 30 by supplying an electrical (e.g., alternating current) signal of a desired frequency to the bottom and top side electrodes 20, 28, then a change in electroacoustic response of the BAW resonator structure may be detected to indicate a presence and/or quantity of analyte bound to the functionalization material 38.

Figure 5:
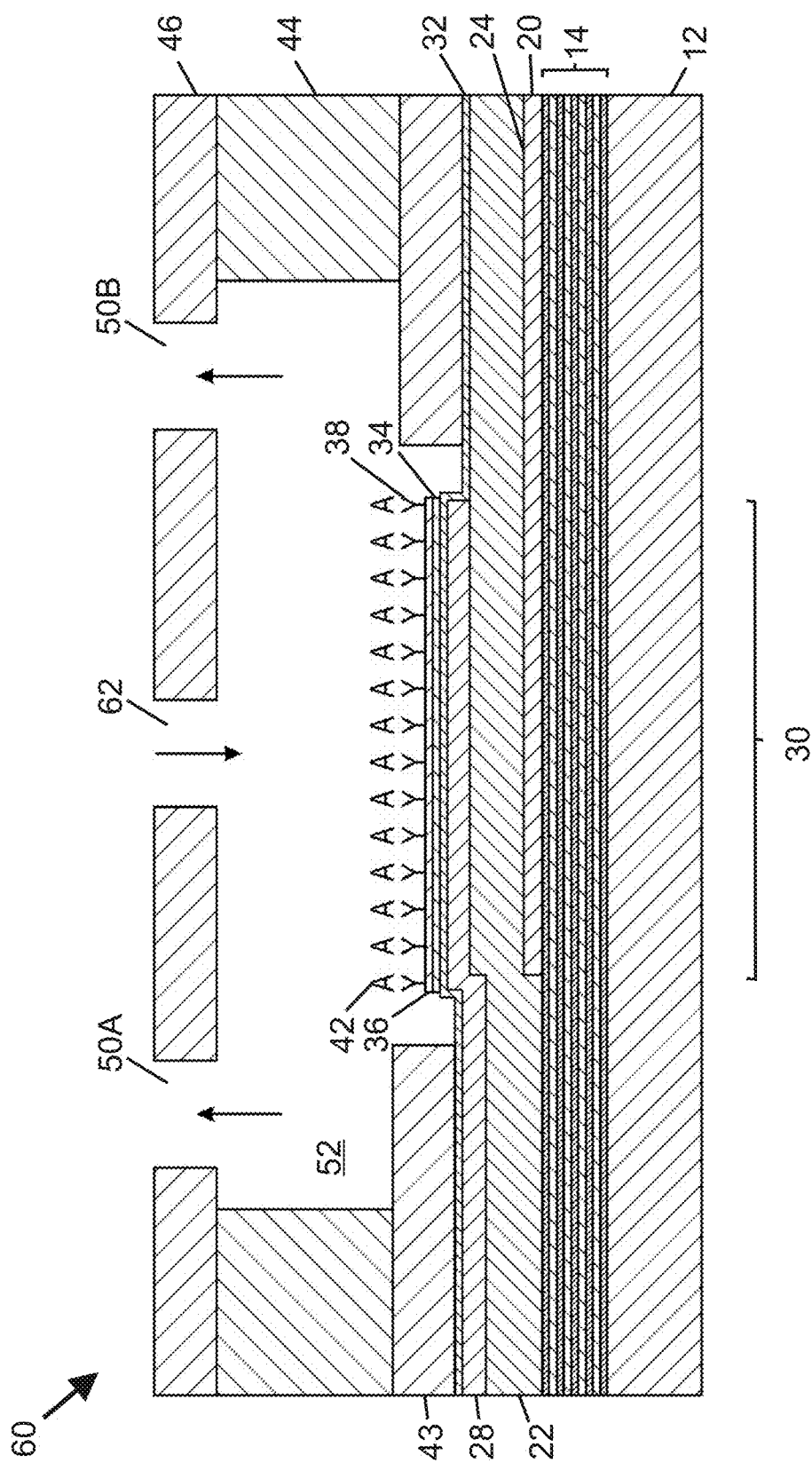
FIG. 5 is a schematic cross-sectional view of a portion of a fluidic device (e.g., a biochemical sensor device) including a fluidic passage bounded from below by a BAW resonator structure, bounded laterally by walls, and bounded from above by a cover or cap layer defining an inlet port and two outlet ports, with a SAM and functionalization material arranged over an active region, with the inlet port arranged above the active region, and with the outlet ports being laterally displaced from the active region.

FIG. 5 is a schematic cross-sectional view of a portion of a fluidic device 60 (e.g., a biochemical sensor device) that is similar to the fluidic device 58 of FIG. 4, but that includes an inlet port 62 arranged above an active region 30, and including two outlet ports 50A, 50B that are laterally displaced from the active region 30. The fluidic device 60 includes a fluidic passage 52 that is bounded from below by a bulk acoustic wave resonator structure including the active region 30, bounded laterally by lower wall-forming layer 43 and walls 44 (which may be formed of stencil layers), and bounded from above by the cover or cap layer 46 defining the inlet port 62 and the outlet ports 50A, 50B. The lower wall-forming layer 43 extends in a medial direction over a hermeticity layer 32, but does not cover the active region 30. The fluidic device 60 includes a substrate 12 overlaid with an acoustic reflector 14, and a bottom side electrode 20 arranged generally below (i.e., along a portion of a lower surface 24 of) the piezoelectric material 22. The active region 30 is defined by a portion of the piezoelectric material 22 arranged between a portion of a top side electrode 28 that overlaps the bottom side electrode 20. The hermeticity layer 32 is arranged over the top side electrode 28 and the piezoelectric material 22. An interface layer 34 and a SAM 36 are provided over a portion of the hermeticity layer 32 that is registered with the active region 30. The SAM 36 is overlaid with a layer of functionalization (e.g., specific binding) material 38 arranged to bind at least one analyte (e.g., analyte 42).

In use of the fluidic device 60, a fluid sample may be supplied through the inlet port 62 into the fluidic passage 52 over the active region 30 to contact the functionalization material 38, and then flow through the outlet ports 50A, 50B to exit the fluidic passage 52. The inlet port 62 is arranged above and registered with the active region 30, and is thereby configured to supply fluid into the fluidic passage 52 in a direction substantially orthogonal to a surface of the active region 30. Such configuration causes fluid to initially flow downward toward a surface of the active region 30 (e.g., to impinge on functionalization material 38 overlying the active region 30) and then change direction to flow laterally through the fluidic passage 52 in a split stream. The change in direction of fluid within the fluidic passage 52 may promote mixing and/or reduce stratification of analyte within the fluid proximate to the active region 30, thereby permitting a rate of binding between the analyte 42 and the functionalization material 38 to be increased relative to the arrangement shown in FIGS. 3 and 4. An increased binding rate may reduce the time necessary to complete measurement of a particular sample. When a bulk acoustic wave having a dominant shear component is induced in the active region 30 by supplying an electrical (e.g., alternating current) signal of a desired frequency to the bottom and top side electrodes 20, 28, then a change in electroacoustic response of the BAW resonator structure may be detected to indicate a presence and/or quantity of analyte 42 bound to the functionalization material 38.

Figure 6:
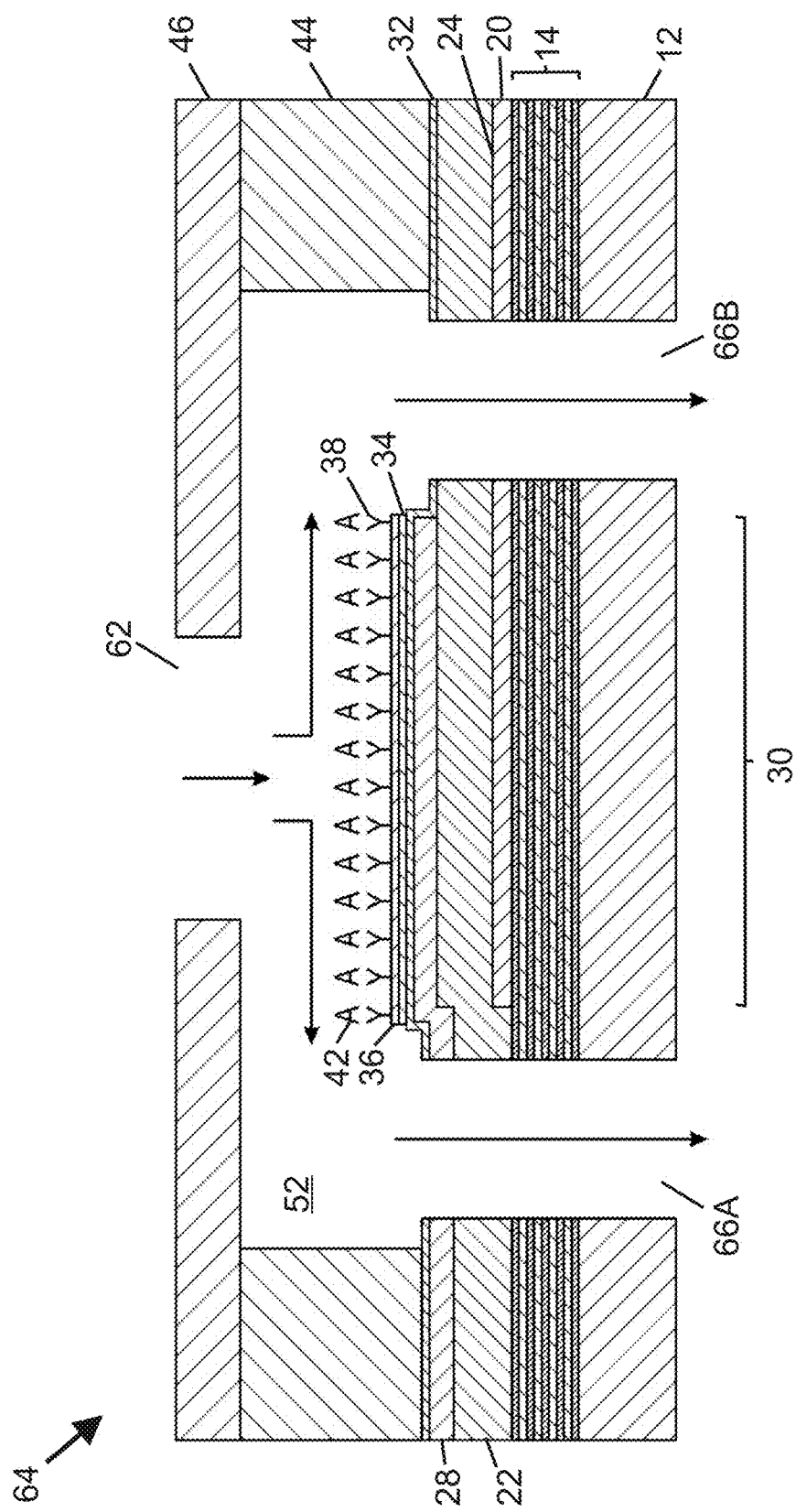
FIG. 6 is a schematic cross-sectional view of a portion of a fluidic device (e.g., a biochemical sensor device) including a fluidic passage bounded from below by a BAW resonator structure, bounded laterally by walls, and bounded from above by a cover or cap layer defining an inlet port, with a SAM and functionalization material arranged over an active region, with the inlet port arranged above the active region, and with two outlet ports defined in the BAW resonator structure.

FIG. 6 is a schematic cross-sectional view of a portion of a fluidic device 64 (e.g., a biochemical sensor device) that is similar to the device 60 of FIG. 5, but that includes outlet ports 66A, 66B defined through a base structure (e.g., including a substrate 12, acoustic reflector 14, and piezoelectric material 22 of a BAW resonator structure), and that includes only a single wall-forming layer (e.g., walls) 44. An inlet port 62 is arranged over and registered with an active region 30 of the BAW resonator structure, and is defined through a cover or cap layer 46 of the fluidic device 64. A fluidic passage 52 is bounded from below by the BAW resonator structure, bounded laterally by walls 44, and bounded from above by the cover or cap layer 46. A bottom side electrode 20 is arranged generally below (i.e., along a portion of a lower surface 24 of) the piezoelectric material 22. The active region 30 is defined by a portion of the piezoelectric material 22 arranged between a portion of a top side electrode 28 that overlaps the bottom side electrode 20. A hermeticity layer 32 is arranged over the top side electrode 28 and the piezoelectric material 22. An interface layer 34 and a SAM 36 are provided over a portion of the hermeticity layer 32 that is registered with the active region 30. The SAM 36 is overlaid with a layer of functionalization (e.g., specific binding) material 38 arranged to bind at least one analyte (e.g., analyte 42).

In use of the fluidic device 64, a fluid sample may be supplied through the inlet port 62 into the fluidic passage 52 over the active region 30 to contact the functionalization material 38, and then flow through the outlet ports 66A, 66B to exit the fluidic passage 52. Arrangement of the inlet port 62 above and registered with the active region 30 causes fluid to be supplied into the fluidic passage 52 in a direction substantially orthogonal to a surface of the active region 30. This causes fluid to initially flow downward toward a surface of the active region 30 (e.g., to impinge on functionalization material 38 overlying the active region 30) and then change direction to flow laterally through the fluidic passage 52 in a split stream. Such arrangement may promote mixing and/or reduce stratification of analyte within the fluid proximate to the active region 30, thereby permitting a rate of binding between analyte 42 and the functionalization material 38 to be increased relative to the arrangement shown in FIGS. 3 and 4. When a bulk acoustic wave having a dominant shear component is induced in the active region 30 by supplying an electrical (e.g., alternating current) signal of a desired frequency to the bottom and top side electrodes 20, 28, then a change in electroacoustic response of the BAW resonator structure may be detected to indicate a presence and/or quantity of analyte 42 bound to the functionalization material 38.

Figure 11:
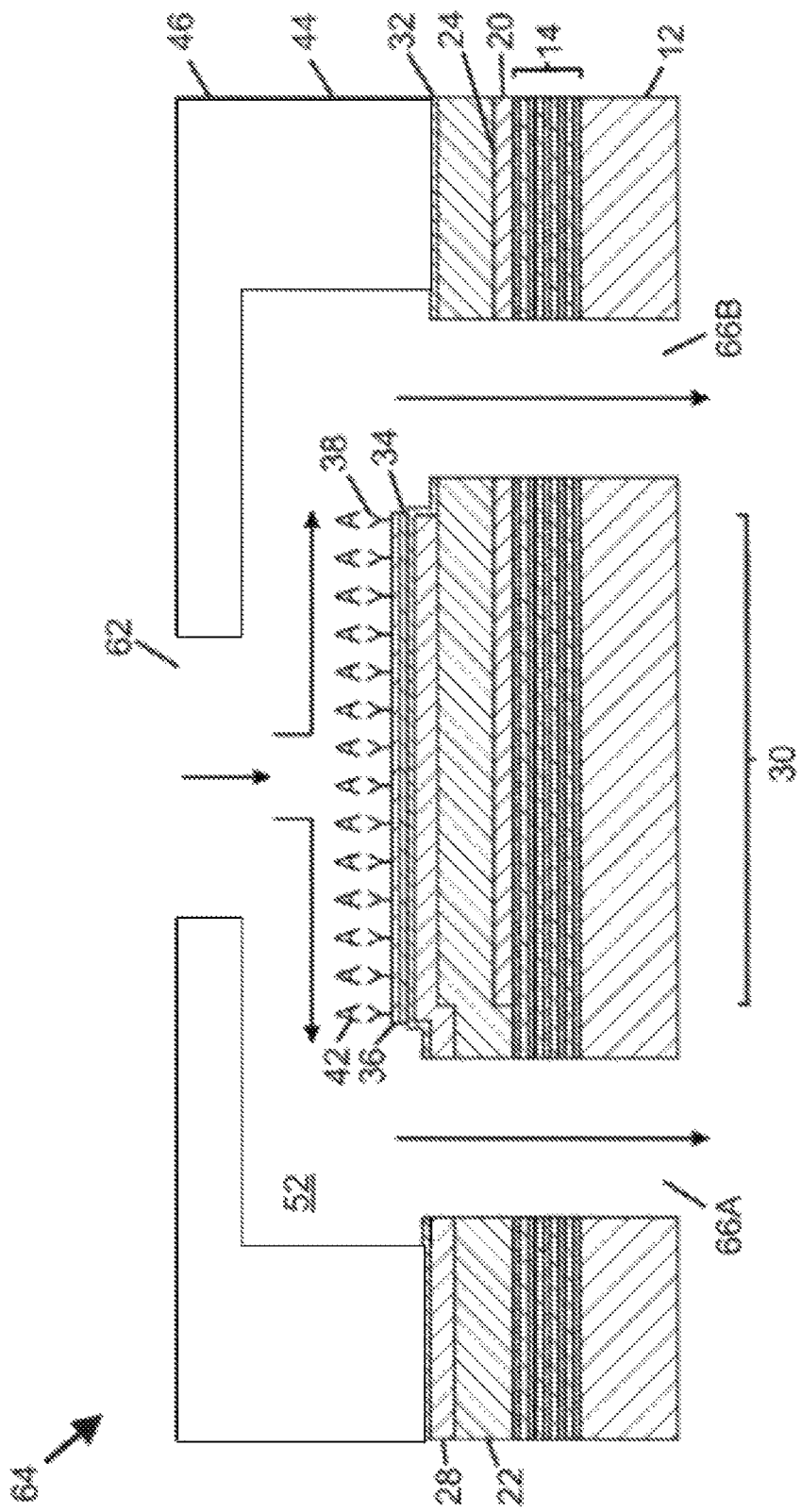
FIG. 11 is a schematic cross-sectional view of a portion of a fluidic device (e.g., a biochemical sensor device) including a fluidic passage bounded from below by a BAW resonator structure, bounded laterally by walls, and bounded from above by a cover or cap layer defining an inlet port, with a SAM and functionalization material arranged over an active region, with the inlet port arranged above the active region, and with two outlet ports defined in the BA W resonator structure.

FIG. 11 is essentially the same as FIG. 6 except that the cover 46 and walls 44 are shown as monolithic in FIG. 11. Reference is made to the discussion above regarding FIG. 6 regarding the numerals used in FIG. 11, as like parts or components are numbered the same.

Figure 7:
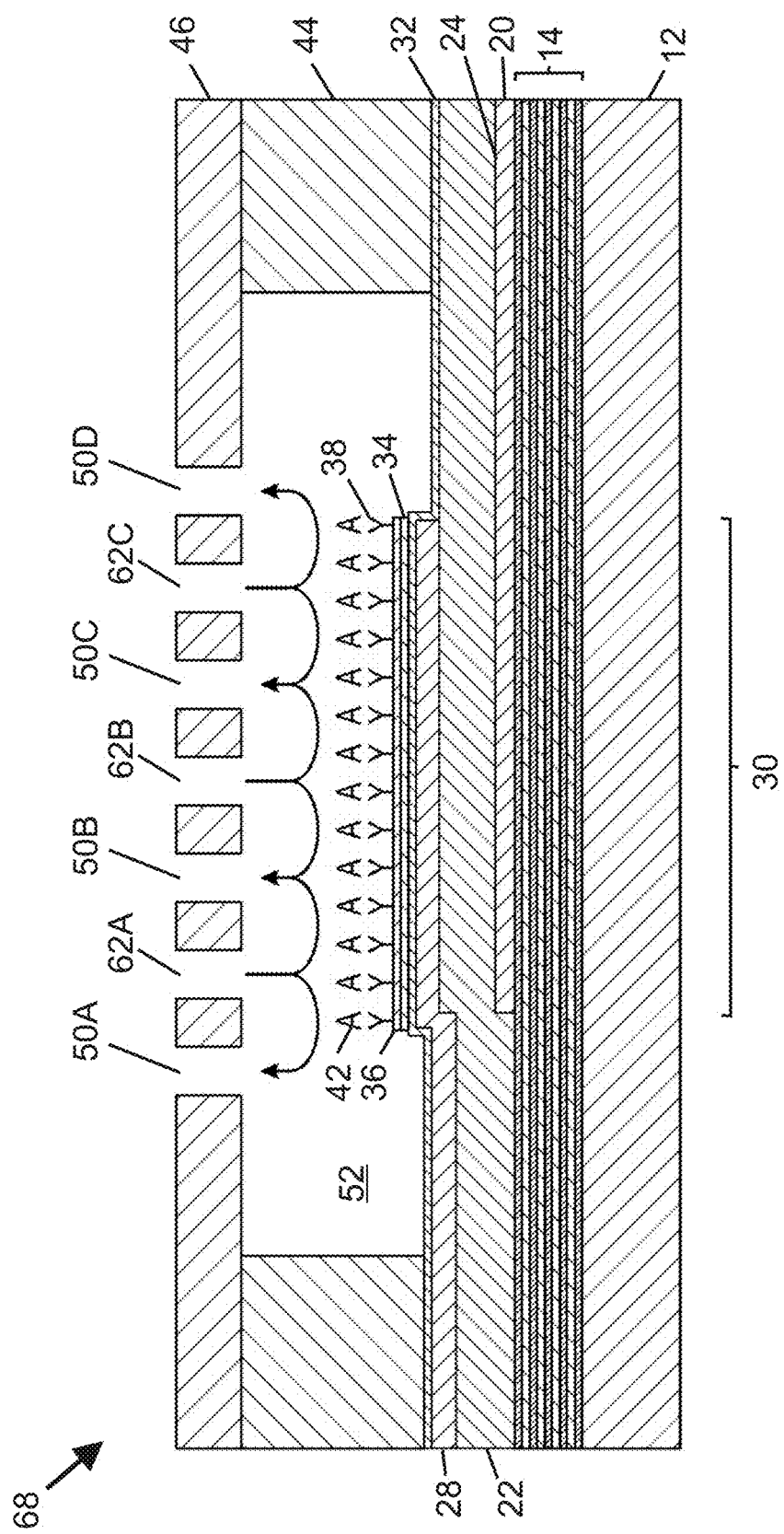
FIG. 7 is a schematic cross-sectional view of a portion of a fluidic device (e.g., a biochemical sensor device) including a fluidic passage bounded from below by a BAW resonator structure, bounded laterally by walls, and bounded from above by a cover or cap layer defining multiple inlet ports and multiple outlet ports, with a SAM and functionalization material arranged over an active region, and with the inlet ports and at least some outlet ports arranged over the active region.

FIG. 7 is a schematic cross-sectional view of a portion of a fluidic device 68 (e.g., a biochemical sensor device) incorporating a BAW resonator structure and including inlet ports 62A-62C and at least some outlet ports 50A-50D arranged over an active region 30 of the BAW resonator structure. The inlet ports 62A-62C and outlet ports 50A-50D are defined in a cover or cap layer 46 that bounds a fluidic passage 52 from above, with the fluidic passage 52 further being bounded from below by a base structure including the BAW resonator structure, and being bounded laterally by walls 44. The base structure includes a substrate 12, an acoustic reflector 14, a piezoelectric material 22, a top side electrode 28, and a bottom side electrode 20. The bottom side electrode 20 is arranged generally below (i.e., along a portion of a lower surface 24 of) the piezoelectric material 22. The active region 30 is defined by a portion of the piezoelectric material 22 arranged between a portion of the top side electrode 28 that overlaps the bottom side electrode 20. A hermeticity layer 32 is arranged over the top side electrode 28 and the piezoelectric material 22. An interface layer 34 and a SAM 36 are provided over a portion of the hermeticity layer 32 that is registered with the active region 30. The SAM 36 is overlaid with a layer of functionalization (e.g., specific binding) material 38 arranged to bind at least one analyte (e.g., analyte 42).

In use of the fluidic device 68, a fluid sample may be supplied through the inlet ports 62A-62C into the fluidic passage 52 over the active region 30 to contact the functionalization material 38, and then flow through the outlet ports 50A-50D to exit the fluidic passage 52. Arrangement of the inlet ports 62A-62C above and registered with the active region 30 causes fluid to be supplied into the fluidic passage 52 in a direction substantially orthogonal to a surface of the active region 30. This causes fluid to initially flow downward toward a surface of the active region 30 (e.g., to impinge on functionalization material 38 overlying the active region 30) and then change direction to ultimately reverse direction and flow upward through the outlet ports 50A-50D. Such arrangement may promote mixing and/or reduce stratification of analyte within the fluid proximate to the active region 30, thereby permitting a rate of binding between analyte 42 and the functionalization material 38 to be increased relative to the arrangement shown in FIGS. 3 and 4. When a bulk acoustic wave having a dominant shear component is induced in the active region 30 by supplying an electrical (e.g., alternating current) signal of a desired frequency to the bottom and top side electrodes 20, 28, then a change in electroacoustic response of the BAW resonator structure may be detected to indicate a presence and/or quantity of analyte 42 bound to the functionalization material 38.

Figure 8A:
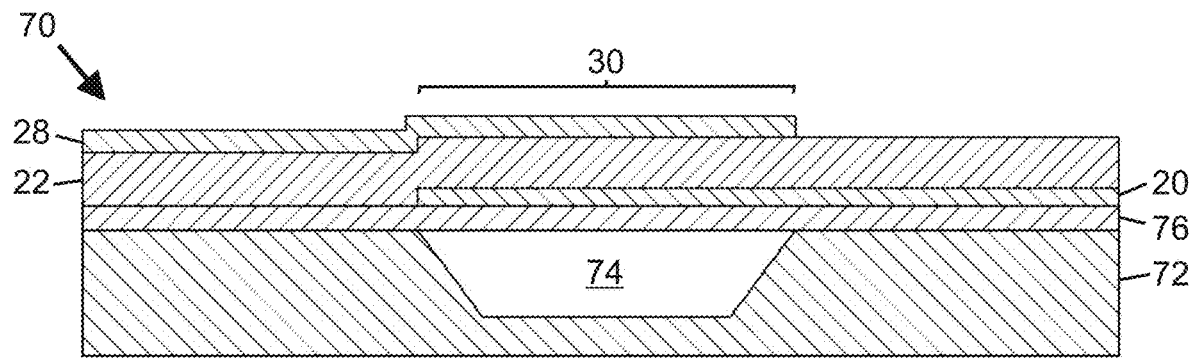
FIG. 8A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity covered by an optional support layer, and an active region registered with the cavity, with a portion of the piezoelectric material arranged between overlapping portions of a top side electrode and a bottom side electrode.

Although the preceding figures illustrate various solidly mounted bulk acoustic wave MEMS resonator structures, it is to be appreciated that film bulk acoustic wave resonator (FBAR) structures may be employed in fluidic devices according to certain embodiments. FIG. 8A is a schematic cross-sectional view of a film bulk acoustic wave resonator (FBAR) structure 70 according to one embodiment including a layer of an inclined c-axis hexagonal crystal structure piezoelectric material 22. The FBAR structure 70 includes a substrate 72 (e.g., silicon or another semiconductor material) defining a cavity 74 optionally covered by a support layer 76 (e.g., silicon dioxide), and includes an active region 30 registered with the cavity 74, with a portion of the piezoelectric material 22 arranged between overlapping portions of a top side electrode 28 and a bottom electrode 20. The bottom side electrode 20 is arranged over a portion of the support layer 76. The bottom side electrode 20 and the support layer 76 are overlaid with the piezoelectric material 22 (e.g., embodying inclined c-axis hexagonal crystal structure piezoelectric material such as AlN or ZnO), and the top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 70. The active region 30 is arranged over and registered with the cavity 74 disposed below the support layer 76. The cavity 74 serves to confine acoustic waves induced in the active region 30 by preventing dissipation of acoustic energy into the substrate 72, since acoustic waves do not efficiently propagate across the cavity 74. In this respect, the cavity 74 provides an alternative to the acoustic reflectors 14 illustrated and described in connection with FIGS. 1 and 3-7. Although the cavity 74 shown is bounded from below by a thinned portion of the substrate 72, in alternative embodiments at least a portion of the cavity 74 extends through an entire thickness of the substrate 72. Steps for forming the FBAR structure 70 may include defining the cavity 74 in the substrate 72, filling the cavity 74 with a sacrificial material (not shown), optionally followed by planarization of the sacrificial material, depositing the support layer 76 over the substrate 72 and the sacrificial material, removing the sacrificial material (e.g., by flowing an etchant through vertical openings defined in the substrate 72 or the support layer 76, or lateral edges of the substrate 72), depositing the bottom side electrode 20 over the support layer 76, growing (e.g., via sputtering or other appropriate methods) the piezoelectric material 22 and depositing the top side electrode 28. In certain embodiments, the top side electrode 28, the piezoelectric material 22, and the bottom side electrode 20 in combination may be self-supporting, and the support layer 76 may be omitted and/or removed by etching in the vicinity of the active region 30.

Figure 8B:
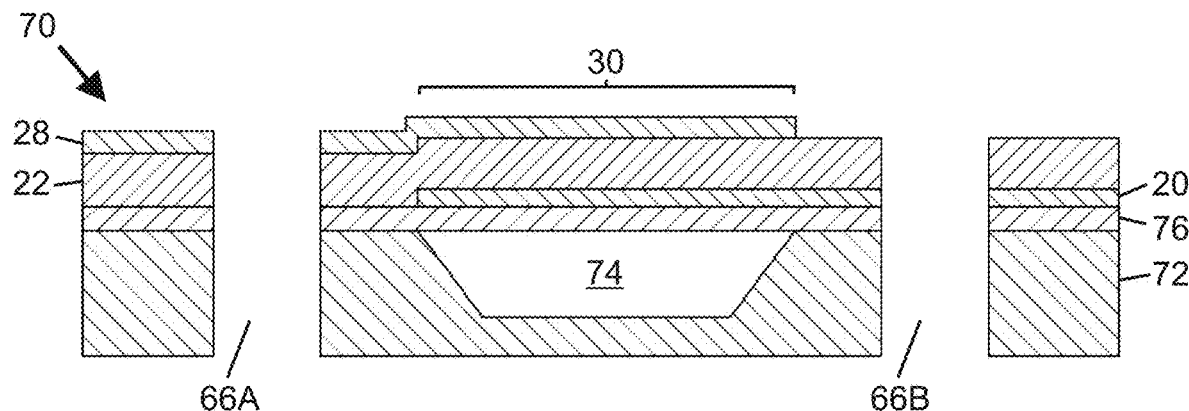
FIG. 8B is a schematic cross-sectional view of the FBAR structure of FIG. 8A with two outlet ports defined through the FBAR structure and laterally offset from the active region.

FIG. 8B is a schematic cross-sectional view of the FBAR structure 70 of FIG. 8A with two outlet ports 66A, 66B defined through the FBAR structure 70 and laterally offset from the active region 30. In certain embodiments, the defining of the outlet ports 66A, 66B through the substrate 72 and the piezoelectric material 22 comprises laser micromachining guided in a water jet. The outlet ports 66A, 66B are laterally offset from the active region 30 as well as the cavity 74 defined in the substrate 72.

Figure 8C:
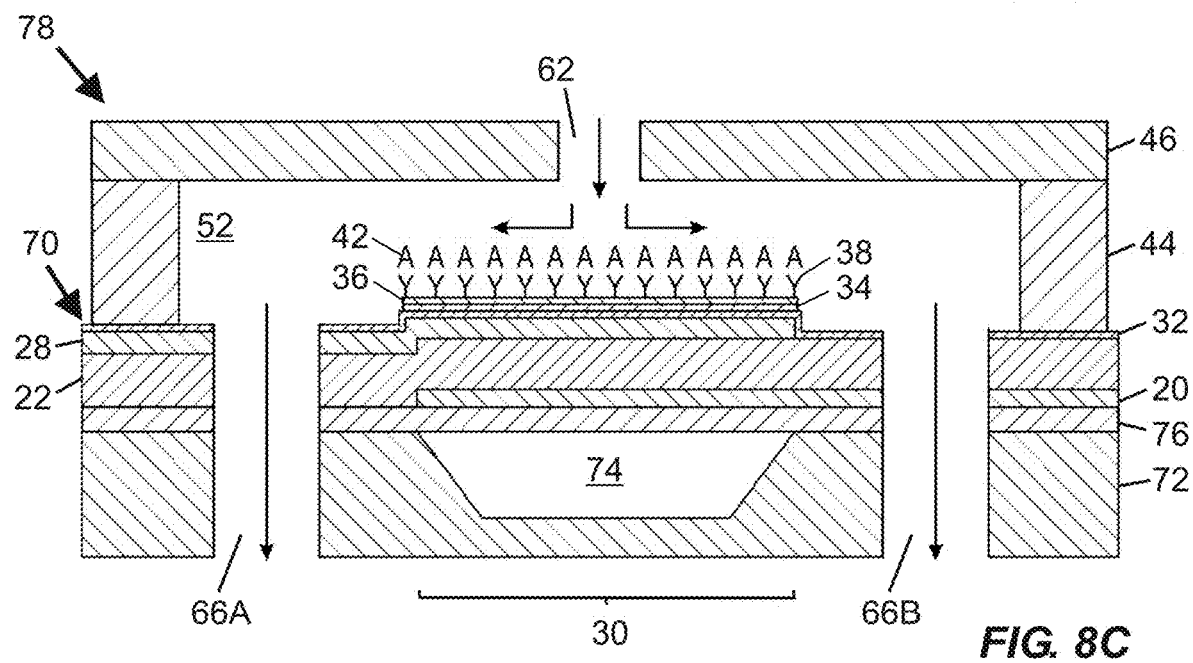
FIG. 8C is a schematic cross-sectional view of a portion of a fluidic device (e.g., a biochemical sensor device) including a fluidic passage bounded from below by the FBAR structure of FIG. 8B, bounded laterally by walls, and bounded from above by a cover or cap layer defining an inlet port, with a SAM and functionalization material arranged over an active region, and with the inlet port being arranged over the active region.

FIG. 8C is a schematic cross-sectional view of a portion of a fluidic device 78 (e.g., a biochemical sensor device) including a fluidic passage 52 bounded from below by the FBAR structure 70 of FIG. 8B, bounded laterally by walls 44, and bounded from above by a cover or cap layer 46 defining an inlet port 62 that is centrally arranged above the active region 30 of the FBAR structure 70. A hermeticity layer 32 is arranged over the top side electrode 28 and the piezoelectric material 22. An interface layer 34 and a SAM 36 are provided over a portion of the hermeticity layer 32 that is registered with the active region 30. The SAM 36 is overlaid with functionalization (e.g., specific binding) material 38. As shown in FIG. 8C, an analyte 42 supplied by the fluid sample is bound to the functionalization material 38. The fluidic device 78 may be used as a sensor to detect presence of a target species in an environment. When a bulk acoustic wave is induced in the active region 30 by supplying an electrical signal (e.g., a radio frequency alternating current signal configured to drive the piezoelectric material 22 in a shear mode) to the bottom and top side electrodes 20, 28, detection of a change in at least one of an amplitude-magnitude property, a frequency property, or a phase property of the FBAR structure 70 indicates a presence and/or quantity of target species (i.e., analyte 42) bound to the functionalization material 38.

In use of the fluidic device 78, a fluid sample may be supplied through the inlet port 62 into the fluidic passage 52 over the active region 30, and then flow through the outlet ports 66A, 66B to exit the fluidic passage 52. Being arranged above and registered with the active region 30, the inlet port 62 is configured to supply fluid in a direction substantially orthogonal to a surface of the active region 30, thereby promoting mixing and/or reducing stratification of analyte within the fluid proximate to the active region 30.

Figure 9:
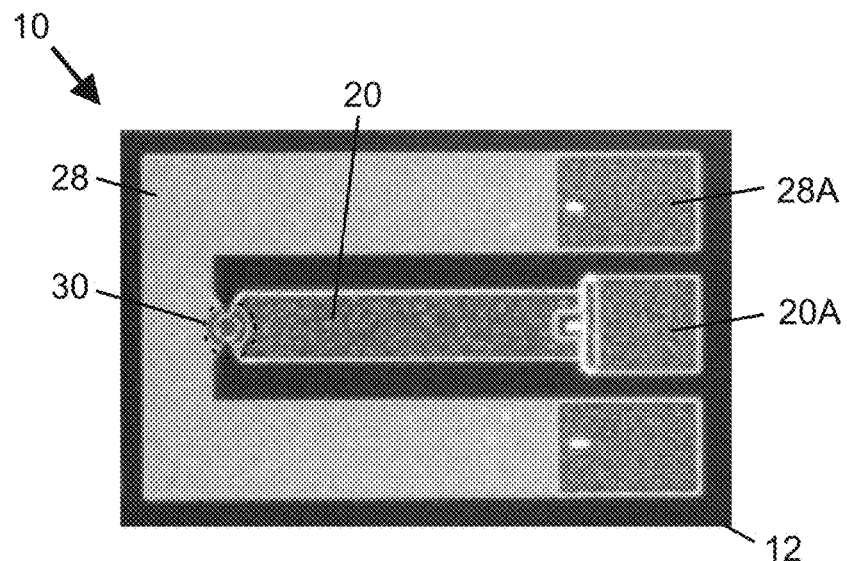
FIG. 9 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 9 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device. If desired, multiple resonator devices 10 may be provided in an array on a single substrate 12.

Figure 10:
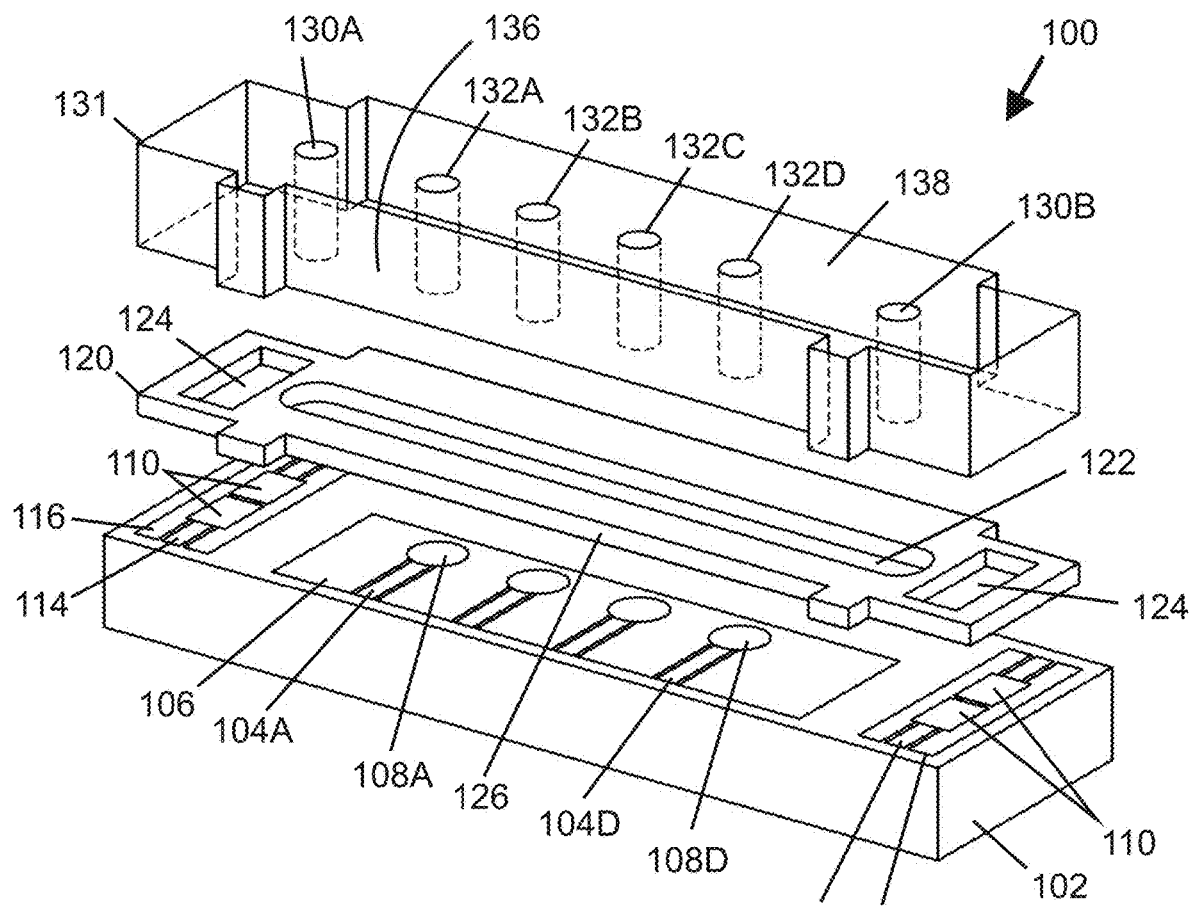
FIG. 10 is a perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer defining multiple inlet ports arranged above the active regions and defining multiple outlet ports laterally displaced from the active regions.

FIG. 10 is a perspective assembly view of a microfluidic device 100 incorporating a substrate 102 with multiple bulk acoustic wave MEMS resonator structures, an intermediate layer 120 defining a central microfluidic channel 122 registered with active regions 108A-108D of the MEMS resonator structures, and a cover or cap layer 131 arranged to cover the intermediate layer 120. The substrate 102 preferably includes an acoustic reflector (not shown) and a piezoelectric material (not shown). Top central portions of the substrate 102 include a top side electrode 106 and bottom side electrodes 104A-104D. Regions in which the foregoing electrodes overlap one another and sandwich the piezoelectric material embody active regions 108A-108D. Preferably, the active regions 108A-108D are overlaid with a hermeticity layer, an interface layer, a self-assembled monolayer, and functionalization (e.g., specific binding) material as disclosed herein. Any suitable number of active regions 108A-108D may be provided and fluidically arranged in series or parallel, although four active regions are illustrated in FIG. 10. Top peripheral (or top end) portions of the substrate 102 further include reference top side electrodes 116 and reference bottom side electrodes 114 in communication with reference overlap regions 110. Such reference overlap regions 110 are not exposed to fluid, and are present to provide a basis for comparing signals obtained from the active regions 108A-108D exposed to fluid within the central microfluidic channel 122.

The substrate 102 is overlaid with the intermediate (e.g., wall-defining) layer 120, wherein the central microfluidic channel 122 is intended to receive fluid, and defines peripheral chambers 124 arranged to overlie the reference overlap regions 110 in a sealed fashion. The intermediate layer 120 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 120 further includes a lateral inset region 126 that enables lateral portions of the top side electrode 106 and bottom side electrodes 104A-104D to be accessed upon assembly of the microfluidic device 100.

The cover or cap layer 131 includes a lateral inset region 136 registered with the lateral inset region 126 of the intermediate layer 120. The cover or cap layer 131 further defines microfluidic inlet ports 132A-132D and microfluidic outlet ports 130A, 130B that are accessible along a top surface 138 of the cover or cap layer 131. The inlet ports 132A-132D are configured to be arranged over and registered with the active regions 108A-108D, whereas the outlet ports 130A, 130B are laterally offset from the active regions 108A-108D and are registered with end portions of the central microfluidic channel 122 defined in the intermediate layer 120. The inlet ports 132A-132D permit fluid (e.g., liquid) to be supplied to the central microfluidic channel 122 over the active regions 108A-108D, with each inlet port 132A-132D being registered with a different active region 108A-108D to permit fluid to be supplied in a direction substantially orthogonal to a surface of each active region 108-108D. Fluid is then transported through the central microfluidic channel 122 to the outlet ports 130A, 130B. Microfluidic devices according to other configurations may be provided, as will be recognized by those skilled in the art upon review of the present disclosure.

Technical benefits obtainable with various embodiments of the present disclosure may include one or more of the following: enhanced rate of analyte binding to functionalization material overlying an active region of a bulk acoustic wave resonator structure, thereby reducing the time required to complete measurement of a particular sample, and/or enhanced mixing of analyte-containing fluids in fluidic devices incorporating bulk acoustic wave resonator structures, including devices suitable for biosensing or biochemical sensing applications.

Those skilled in the art will recognize improvements and modifications to the preferred embodiments of the present disclosure. All such improvements and modifications are considered within the scope of the concepts disclosed herein and the claims that follow.

What is claimed is:

1. A fluidic device comprising:
a base structure comprising: (i) a substrate; (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and (iii) at least one functionalization material arranged over at least a portion of the active region;
a wall structure arranged over at least a portion of the base structure and defining lateral boundaries of a fluidic passage arranged to receive a fluid and containing the active region; and
a cover structure arranged over the wall structure and defining an upper boundary of the fluidic passage;
wherein the cover structure defines at least one first port that is in fluid communication with the fluidic passage, and at least a portion of the at least one first port is registered with the active region to cause fluid to enter the fluidic passage in a direction normal to a surface of the active region.

2. The fluidic device of claim 1, wherein the wall structure and the cover structure are embodied in a monolithic body structure.

3. The fluidic device of claim 1, wherein the cover structure comprises a cover layer, the wall structure comprises at least one wall layer, and the at least one wall layer is arranged between the base structure and the cover layer.

4. The fluidic device of claim 1, further comprising at least one second port that is in fluid communication with the fluidic passage, wherein the at least one second port is defined through the cover structure.

5. The fluidic device of claim 1, further comprising a plurality of second ports in fluid communication with the fluidic passage, wherein each second port of the plurality of second ports is laterally displaced relative to the at least one first port.

6. The fluidic device of claim 1, wherein the at least one bulk acoustic wave resonator structure comprises a plurality of bulk acoustic wave resonator structures.

7. The fluidic device of claim 1, wherein the base structure further comprises at least one acoustic reflector element arranged between the substrate and the at least one bulk acoustic wave resonator structure.

8. The fluidic device of claim 1, wherein the at least one functionalization material comprises a specific binding material.

9. The fluidic device of claim 1, wherein the at least one functionalization material comprises a non-specific binding material.

10. The fluidic device of claim 1, further comprising a self-assembled monolayer arranged between the at least one functionalization material and the top side electrode.

11. The fluidic device of claim 10, further comprising an interface layer arranged between the self-assembled monolayer and the top side electrode.

12. The fluidic device of claim 11, further comprising a hermeticity layer arranged between the interface layer and the top side electrode.

* * * * *